United States Patent
Löffler et al.

(10) Patent No.: US 7,022,791 B2
(45) Date of Patent: *Apr. 4, 2006

(54) COSMETIC, PHARMACEUTICAL AND DERMATOLOGICAL PRODUCTS CONTAINING AN ELECTROLYTE

(75) Inventors: Matthias Löffler, Niedernhausen (DE); Roman Morschhäuser, Mainz (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/433,205

(22) PCT Filed: Nov. 28, 2001

(86) PCT No.: PCT/EP01/13868

§ 371 (c)(1), (2), (4) Date: Nov. 17, 2003

(87) PCT Pub. No.: WO02/44267

PCT Pub. Date: Jun. 6, 2002

(65) Prior Publication Data

US 2004/0115149 A1  Jun. 17, 2004

(30) Foreign Application Priority Data

Dec. 1, 2000  (DE) ............... 100 59 824

(51) Int. Cl.
*C08L 33/00* (2006.01)

(52) U.S. Cl. .............. 526/288; 526/277; 526/250; 526/303.1; 526/307.1; 526/307.2; 526/279; 526/287; 525/291; 514/937; 514/772.4; 424/70.2; 424/70.21

(58) Field of Classification Search .............. 424/70.2, 424/70.21; 242/70.21; 514/937, 772.4; 525/291; 526/288, 277, 250, 303.1, 307.1, 526/307.2, 279, 287

See application file for complete search history.

(56) References Cited

U.S. PATENT DOCUMENTS

| 5,104,645 A | | 4/1992 | Cardin et al. ............... 424/70 |
| 5,510,100 A | * | 4/1996 | Picard et al. ............... 424/59 |
| 6,123,960 A | | 9/2000 | Favre et al. ............... 424/450 |
| 6,645,476 B1 | * | 11/2003 | Morschhauser et al. ... 424/70.1 |
| 2003/0108497 A1 | | 6/2003 | Chevalier |
| 2004/0024154 A1 | | 2/2004 | Schinabeck |

FOREIGN PATENT DOCUMENTS

| EP | 1 026 219 | | 8/2000 |
| EP | 1069142 | * | 1/2001 |
| WO | WO 00/07638 | | 2/2000 |
| WO | WO 01/96422 | | 12/2001 |

OTHER PUBLICATIONS

Research Disclosure 415006, Recearch disclosure Journal No. 41506, Nov. 1998.*

* cited by examiner

*Primary Examiner*—Irina S. Zemel
(74) *Attorney, Agent, or Firm*—Richard P. Silverman

(57) ABSTRACT

The invention relates to cosmetic, dermatological, and pharmaceutical products containing an electrolyte. The products are obtained by free-radical copolymerization of A) acryloyldimethyltaurine and/or acryloyldimethyltaurates, and
B) optionally, one or more further olefinically unsaturated, noncationic comonomers,
C) optionally, one or more olefinically unsaturated, cationic comonomers,
D) optionally, one or more silicon-containing component(s),
E) optionally, one or more fluorine-containing component(s),
F) optionally, one or more macromonomers,
G) optionally, the copolymerization taking place in the presence of at least one polymeric additive,
H) with the proviso that component A) is copolymerized with at least one component selected from one of the groups D) to G).

44 Claims, No Drawings

COSMETIC, PHARMACEUTICAL AND DERMATOLOGICAL PRODUCTS CONTAINING AN ELECTROLYTE

The present invention relates to electrolyte-containing cosmetic, pharmaceutical, and dermatological compositions comprising comb copolymers based on acryloyldimethyltaurine.

Consumer desires and cosmetic product rheology are closely interlinked. Thus, for example, the visual appearance of a cream or lotion is influenced by the viscosity. The sensorial properties, such as consistency or spreadability, determine the individual profile of a cosmetic product. The storage stability of the formulation as well, an example being that of pearlescent shampoos or oil-containing body washes, depends closely on the Theological properties of the product.

Furthermore, a liquid surfactant system must also have a viscosity which is adapted to the particular end use and which can to a great extent be varied. Thus the viscosity is a decisive criterion of the quality of a liquid surfactant preparation. A shower gel, for example, is required to have relatively high viscosities, while a hair shampoo commonly constitutes a flowable liquid having a relatively low viscosity.

In the cosmetics sector, therefore, polyelectrolytes have a leading role as thickeners and gel formers. State of the art are, in particular, the polyacrylic acids prepared on the basis of poly(meth)acrylic acid, and the water-soluble copolymers thereof. The diversity of possible structures and the diverse possibilities for application which they entail are manifested not least in a multiplicity of new patents filed worldwide since the mid-1970s. A substantial disadvantage of these poly(meth)acrylic acid-based thickeners is the heavy pH dependency of the thickening action. Thus, in general, viscosity is only developed when the pH of the formulation is adjusted to above 6 so that the poly(meth)acrylic acid is in neutralized form. Furthermore, the corresponding gels/formulations are sensitive to UV radiation and also to shearing, and, moreover, impart a sticky sensation on the skin. The handling of these thickener polymers is also ripe for improvement: since the thickeners based on poly(meth)acrylic acid are generally present in acidic form, their formulation requires an additional neutralizing step. Another serious drawback of the thickeners based on poly(meth)acrylic acid is a very high sensitivity toward electrolytes. As soon as aqueous systems (gels, emulsions, etc.) containing polyelectrolytes come into contact with salt there is a dramatic decrease in the viscosity. This reduction in viscosity is explained by a shielding of the ionic centers in the polymer by the electrolyte, leading to collapse of the polymer network structure. Moreover, the aqueous systems containing polyelectrolytes become cloudy on contact with salt.

Thickening of electrolyte-containing aqueous surfactant systems therefore takes place in general by addition of cellulose derivatives, natural polymers (e.g., xanthan gum, guar), nonionic surfactants or polyethylene glycol derivatives.

All of these thickener systems lead to surfactant systems which are pseudoplastic and/or thixotropic. Depending on thickener, however, a variety of drawbacks must be accepted:

The thickening action of many cellulose derivatives is severely reduced by salt. Natural polymers are very difficult to process, and clear formulations are frequently impossible to realize.

Known nonionic thickeners for liquid surfactant formulations include fatty acid alkanol amides. The preferred fatty acid alkanol amide used in practice is coconut fatty acid diethanol amide. It exhibits the best thickening properties as compared with other fatty acid diethanol amides. A drawback, however, is the presence of amine-type secondary compounds/contaminants.

Polyethylene glycol derivatives such as PEG 6000 distearate, PEG-120 methyl glucose dioleate, PEG-150 pentaerythrityl tetrastearate, PEG-20 methyl glucose sesquistearate, etc., are not only complex to prepare (deficient conformity from one batch to the next), but also in some cases complicated to process (melting or dissolution at high temperature, high quantities to be used).

There is therefore a need for polymers which ensure outstanding thickener performance even in the presence of electrolytes, which are easy to process, which can be used over a broad pH range, and which exhibit outstanding Theological and sensorial properties in conjunction with effective stability. A further object which arose was to find additives suitable for viscosity adjustment in surfactant formulations, which preferably give clear solutions, which can be used universally and at low concentration, and which, furthermore, are toxicologically unobjectionable.

Surprisingly it has now been found that a new class of comb copolymers based on acryloyldimethyltaurine—and suitable in the capacity of a thickener, bodying agent, emulsifier, dispersant, lubricant, conditioner and/or stabilizer—are outstandingly suitable for use in electrolyte-containing cosmetic, pharmaceutical, and dermatological compositions.

The invention accordingly provides electrolyte-containing cosmetic, dermatological, and pharmaceutical compositions comprising at least one copolymer obtainable by free-radical copolymerization of A) acryloyldimethyltaurine and/or acryloyldimethyltaurates, B) if desired, one or more further olefinically unsaturated, noncationic, optionally crosslinking comonomers which have at least one oxygen, nitrogen, sulfur or phosphorus atom and possess a molecular weight of less than 500 g/mol, C) if desired, one or more olefinically unsaturated, cationic comonomers which have at least one oxygen, nitrogen, sulfur or phosphorus atom and possess a molecular weight of less than 500 g/mol, D) if desired, one or more silicon-containing components capable of free-radical polymerization and having a functionality of at least one, E) if desired, one or more fluorine-containing components capable of free-radical polymerization and having a functionality of at least one, F) if desired, one or more olefinically mono- or polyunsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E), G) the copolymerization taking place if desired in the presence of at least one polymeric additive having number-average molecular weights of from 200 g/mol to $10^9$ g/mol, H) with the proviso that component A) is copolymerized with at least one component selected from one of the groups D) to G).

The copolymers of the invention preferably possess a molecular weight of from $10^3$ g/mol to $10^9$ g/mol, more preferably from $10^4$ to $10^7$ g/mol, with particular preference from $5*10^4$ to $5*10^6$ g/mol.

The acryloyldimethyltaurates can be the organic or inorganic salts of acryloyldimethyltaurine. Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1–C_{22})$-alkyl radicals or $(C_2–C_{10})$-hydroxyalkyl radicals. Preference is also given to mono- to triethoxylated ammonium compounds with different degrees of ethoxylation. It should be noted that mixtures of two or more of the abovementioned representatives are also embraced by the invention.

The degree of neutralization of the acryloyldimethyltaurine can be between 0 and 100%, with particular preference being given to a degree of neutralization of more than 80%.

Based on the total mass of the copolymers, the amount of acryloyidimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyldimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 30.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkylammonium, dialkylammonium, trialkylammonium and/or tetraalkylammonium radicals, in which the alkyl substituents of the amines independently of one another can be $(C_1–C_{22})$-alkyl radicals or $(C_2–C_{10})$-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl] succinate; N,N-dimethylamino methacrylate; diethylaminomethyl methacrylate; acrylamido- and methacrylamido-glycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable comonomers C) include all olefinically unsaturated monomers with cationic charge which are capable of forming copolymers with acryloyldimethyltaurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine, zwitterionic or amphoteric structure.

Comonomers C) for the purposes of the invention are also amino-functionalized precursors which can be converted by polymer-analogous reactions into their corresponding quaternary derivatives (e.g., reaction with dimethyl sulfate, methyl chloride), zwitterionic derivatives (e.g., reaction with hydrogen peroxide), betaine derivatives (e.g., reaction with chloroacetic acid), or amphoteric derivatives.

Particularly preferred comonomers C) are
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl4-vinylpyridinium chloride,
dimethylaminoethyl methacrylate,
dimethylaminopropylmethacrylamide,
methacryloylethyl N-oxide and/or
methacryloylethylbetaine.

The weight fraction of the comonomers C), based on the total mass of the copolymers, can be from 0.1 to 99.8% by weight, more preferably from 0.5 to 30% by weight, and very preferably from 1 to 20% by weight.

Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicone-containing components are those of formula (I)

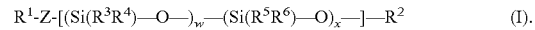

$$R^1\text{-}Z\text{-}[(Si(R^3R^4)\text{—}O\text{—})_w\text{—}(Si(R^5R^6)\text{—}O)_x\text{—}]\text{—}R^2 \qquad (I).$$

In this formula $R^1$ represents a polymerizable function from the group of the vinylically unsaturated compounds which is suitable for the synthesis of polymeric structures by a free-radical route. $R^1$ represents preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

The attachment of the silicone-containing polymer chain to the reactive end group $R^1$ requires a suitable chemical bridge Z. Preferred bridges Z are —O—, —(($C_1$–$C_{50}$) alkylene)—, —(($C_6$–$C_{30}$)arylene)—, —(($C_5$–$C_8$)cycloalkylene)—, —(($C_1$–$C_{50}$)alkenylene)—, —(polypropylene oxide)$_n$-, —(polyethylene oxide)$_o$-, —(polypropylene oxide)$_n$(polyethylene oxide)$_o$-, where n and o independently of one another denote numbers from 0 to 200 and the distribution of the EO/PO units can be random or in the form of blocks. Further suitable bridge groups Z are —((C$_1$–C$_{10}$)alkyl)-(Si(OCH$_3$)$_2$)— and —(Si(OCH$_3$)$_2$)—.

The polymeric central moiety is represented by silicone-containing repeating units. The radicals R$^3$, R$^4$, R$^5$, and R$^6$ denote independently of one another —CH$_3$, —O—CH$_3$, —C$_6$H$_5$ or —O—C$_6$H$_5$.

The indices w and x represent stoichiometric coefficients which amount independently of one another to from 0 to 500, preferably 10 to 250.

The distribution of the repeating units across the chain can be not only purely random but also blocklike, alternating or gradientlike.

R$^2$ can first be an aliphatic, olefinic, cycloaliphatic, arylaliphatic or aromatic (C$_1$–C$_{50}$) hydrocarbon radical (linear or branched) or —OH, —NH$_2$, —N(CH$_3$)$_2$, —R$^7$ or stand for the structural unit [-Z-R$^1$]. The definition of the two variables Z and R$^1$ has already been explained. R$^7$ stands for further Si-containing groups. Preferred radicals R$^7$ are —O—Si(CH$_3$)$_3$, —O—Si(Ph)$_3$, —O—Si(O—Si(CH$_3$)$_3$)$_2$CH$_3$) and —O—Si(O—Si(Ph)$_3$)$_2$Ph).

If R$^2$ is an element of the group [-Z-R$^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following components with acrylic or methacrylic modification:

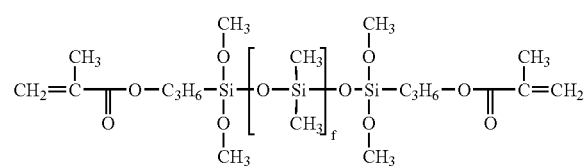

methacryloyloxypropyldimethylsilyl-endblocked polydimethylsiloxanes (f=2 to 500)

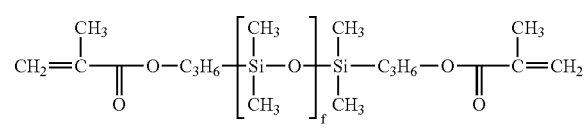

methacryloyloxypropyl-endblocked polydimethylsiloxanes (f=2 to 500)

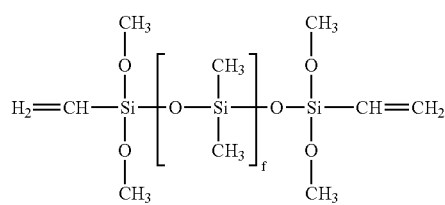

vinyldimethoxysilyl-endblocked polydimethylsiloxanes (f=2–500).

Based on the total mass of the copolymers, the amount of silicon-containing components can be up to 99.8% by weight, preferably from 0.5 to 30% by weight, more preferably from 1 to 20% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked.

Preferred fluorine-containing components E) are those of formula (II)

$$R^1—Y—C_rH_{2r}C_sF_{2s}CF_3 \quad (II)$$

In this formula R$^1$ represents a polymerizable function from the group of the vinylically unsaturated compounds which is suitable for the construction of polymeric structures by a free-radical route. R$^1$ is preferably a vinyl, allyl, methallyl, methylvinyl, acryloyl (CH$_2$=CH—CO—), methacryloyl (CH$_2$=C[CH$_3$]—CO—), crotonyl, senecionyl, itaconyl, maleyl, fumaryl or styryl radical, more preferably an acryloyl or methacryloyl radical.

The attachment of the fluorine-containing group to the reactive end group R$^1$ requires a suitable chemical bridge Y. Preferred bridges Y are —O—, —C(O)—, —C(O)—O—, —S—, —O—CH$_2$—CH(O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—(C$_1$–C$_{50}$)alkyl-O—, —O-phenyl-O—, —O-benzyl-O—, —O-(C$_5$–C$_8$)cycloalkyl-O—, —O-(C$_1$–C$_{50}$)alkenyl-O—, —O—(CH(CH$_3$)—CH$_2$—O)$_n$—, —O—(CH$_2$—CH$_2$—O)$_n$—, and —O—([CH—CH$_2$—O]$_n$—[CH$_2$—CH$_2$—O]$_m$)$_o$—, where n, m, and o independently of one another denote numbers from 0 to 200 and the distribution of the EO and PO units can be random or in the form of blocks. r and s are stoichiometric coefficients which independently of one another denote numbers from 0 to 200.

Preferred fluorine-containing components E) of formula (II) are
perfluorohexylethanol methacrylate,
perfluorohexoylpropanol methacrylate,
perfluoroctylethanol methacrylate,
perfluoroctylpropanol methacrylate,
perfluorohexylethanolyl polyglycol ether methacrylate,
perfluorohexoylpropanolyl poly[ethylglycol-co-propylene glycol ether]acrylate,
perfluoroctylethanolyl poly[ethylglycol-block-co-propylene glycol ether]methacrylate,
perfluoroctylpropanolyl polypropylene glycol ether methacrylate.

Based on the total mass of the copolymers the amount of fluorine-containing components can be up to 99.9% by weight, preferably from 0.5 to 30% by weight, more preferably from 1 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers.

Preferred macromonomers F) are compounds of formula (III)

$$R^1\text{-}Y\text{-}[(A)_v\text{-}(B)_w\text{-}(C)_x\text{-}(D)_z]\text{-}R^2 \quad (III)$$

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

Attachment of the polymer chain to the reactive end group requires a suitable bridging group Y. Preferred bridges Y are —O—, —C(O)—, —C(O)—O—, —S—, —O—$CH_2$—CH(O—)—$CH_2$OH, —O—$CH_2$—CH(OH)—$CH_2$O—, —O—$SO_2$—O—, —O—$SO_2$—O—, —O—SO—O—, —PH—, —P($CH_3$)—, —$PO_3$—, —NH—, and —N($CH_3$)—, more preferably —O—.

The polymeric central moiety of the macromonomer is represented by the discrete repeating units A, B, C, and D. Preferably the repeating units A, B, C, and D are derived from: acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D. v, w, x, and z amount independently of one another to from 0 to 500, preferably 1 to 30, it being necessary for the sum of the four coefficients on average to be $\geq 1$.

The distribution of the repeating units over the macromonomer chain can be random, blocklike, alternating or gradientlike.

$R^2$ denotes a linear or branched aliphatic, olefinic, cycloaliphatic, arylaliphatic or aromatic ($C_1$–$C_{50}$) hydrocarbon radical, OH, —$NH_2$, —N($CH_3$)$_2$ or is the structural unit [—Y—$R^1$].

In the case of $R^2$ being [—Y—$R^1$] the macromonomers in question are difunctional and suitable for crosslinking the copolymers.

Particularly preferred macromonomers F) are acrylically or methacrylically monofunctionalized alkyl ethoxylates of formula (IV).

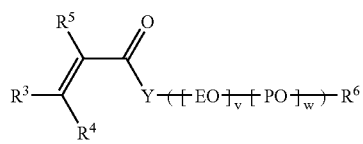
(IV)

$R_3$, $R_4$, $R_5$, and $R_6$ are independently of one another hydrogen or n-aliphatic, iso-aliphatic, olefinic, cycloaliphatic, arylaliphatic or aromatic ($C_1$–$C_{30}$) hydrocarbon radicals.

Preferably $R_3$ and $R_4$ are H or —$CH_3$, more preferably H; $R_5$ is H or —$CH_3$; and $R_6$ is an n-aliphatic, iso-aliphatic, olefinic, cycloaliphatic, arylaliphatic or aromatic ($C_1$–$C_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the above-mentioned bridges.

Further particularly preferred macromonomers F) have the following structure in accordance with formula (IV):

| Name | $R^3$ | $R^4$ | $R^5$ | $R^6$ | v | w |
|---|---|---|---|---|---|---|
| ® LA-030 methacrylate | H | H | —$CH_3$ | -lauryl | 3 | 0 |
| ® LA-070 methacrylate | H | H | —$CH_3$ | -lauryl | 7 | 0 |
| ® LA-200 methacrylate | H | H | —$CH_3$ | -lauryl | 20 | 0 |
| ® LA-250 methacrylate | H | H | —$CH_3$ | -lauryl | 25 | 0 |
| ® T-080 methacrylate | H | H | —$CH_3$ | -talc | 8 | 0 |
| ® T-080 acrylate | H | H | H | -talc | 8 | 0 |
| ® T-250 methacrylate | H | H | —$CH_3$ | -talc | 25 | 0 |
| ® T-250 crotonate | —$CH_3$ | H | —$CH_3$ | -talc | 25 | 0 |
| ® OC-030 methacrylate | H | H | —$CH_3$ | -octyl | 3 | 0 |
| ® OC-105 methacrylate | H | H | —$CH_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | —$CH_3$ | —$CH_3$ | H | -behenyl | 10 | 0 |
| ® PEG-440 diacrylate | H | H | H | -acryloyl | 10 | 0 |
| ® B-11-50 methacrylate | H | H | —$CH_3$ | -butyl | 17 | 13 |
| ® MPEG-750 methacrylate | H | H | —$CH_3$ | -methyl | 18 | 0 |
| ® P-010 acrylate | H | H | H | -phenyl | 10 | 0 |
| ® O-050 acrylate | H | H | H | -oleyl | 5 | 0 |

Further particularly suitable macromonomers F) are esters of (meth)acrylic acid with ($C_{10}$–$C_{18}$) fatty alcohol polyglycol ethers having 8 EO units (Genapol® C-080)

$C_{11}$ oxo alcohol polyglycol ethers having 8 EO units (Genapol® UD-080)

($C_{12}$–$C_{14}$) fatty alcohol polyglycol ethers having 7 EO units (Genapol® LA-070)

($C_{12}$–$C_{14}$) fatty alcohol polyglycol ethers having 11 EO units (Genapol® LA-110)

($C_{16}$–$C_{18}$) fatty alcohol polyglycol ethers having 8 EO units (Genapol® T-080)

($C_{16}$–$C_{18}$) fatty alcohol polyglycol ethers having 15 EO units (Genapol® T-150)

($C_{16}$–$C_{18}$) fatty alcohol polyglycol ethers having 11 EO units (Genapol® T-110)

($C_{16}$–$C_{18}$) fatty alcohol polyglycol ethers having 20 EO units (Genapol® T-200)

($C_{16}$–$C_{18}$) fatty alcohol polyglycol ethers having 25 EO units (Genapol® T-250)

($C_{18}$–$C_{22}$) fatty alcohol polyglycol ethers having 25 EO units and/or iso-($C_{16}$–$C_{18}$) fatty alcohol polyglycol ethers having 25 EO units.

The Genapol® grades are products of Clariant GmbH.

The molecular weight of the macromonomers F) is preferably from 200 g/mol to $10^6$ g/mol, more preferably from 150 to $10^4$ g/mol, and very preferably from 200 to 5 000 g/mol.

Based on the total mass of the copolymers it is possible for the amount of macromonomers to be up to 99.9% by weight. The ranges used are preferably from 0.5 to 30% by weight and from 70 to 99.5% by weight. Particularly preferred are ranges from 1 to 20% by weight and from 75 to 95% by weight.

Preferred copolymers are those obtainable by copolymerizing at least components A), C) and D).

Further preferred copolymers are those obtainable by copolymerizing at least components A), C) and E).

Further preferred copolymers are those obtainable by copolymerizing at least components A), C) and F).

Further preferred copolymers are those obtainable by copolymerizing at least components A), B) and F).

Further preferred copolymers are those obtainable by copolymerizing at least components A), D) and F).

Further preferred copolymers are those obtainable by copolymerizing at least components A) and F).

Further preferred copolymers are those obtainable by copolymerizing at least components A) and D).

Further preferred copolymers are those obtainable by copolymerizing at least components A) and E).

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention. Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols, preferably in t-butanol. The term "copolymers" also comprehends those having more than two different monomer types.

Particularly preferred additives G) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]trimethylammonium chloride (MAPTAC); polyalkylene glycols and/or alkylpolyglycols.

Particularly preferred additives G) are polyvinylpyrrolidones (e.g., Luviskol K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

In another preferred embodiment the copolymers of the invention are crosslinked, i.e., they contain comonomers having at least two polymerizable vinyl groups. Preferred crosslinkers are methylenebisacrylamide; methylenebismethacrylamide; esters of unsaturated monocarboxylic and polycarboxylic acids with polyols, preferably diacrylates and triacrylates, dimethacrylates and trimethacrylates, more preferably butanediol and ethylene glycol diacrylate and methacrylate, trimethylolpropane triacrylate (TMPTA) and trimethylolpropane trimethacrylate (TMPTMA); allyl compounds, preferably ailyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. A particularly preferred crosslinker is trimethylolpropane triacrylate (TMPTA). The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electromagnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example.

Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

Serving as the polymerization medium may be any solvents which are very substantially inert in respect of free-radical polymerization reactions and which allow the development of high molecular weights. Use is preferably made of water and lower, tertiary alcohols or hydrocarbons having 3 to 30 carbon atoms. In one particularly preferred embodiment t-butanol is used as the reaction medium. Mixtures of two or more representatives of the potential solvents described are of course likewise in accordance with the invention. This also includes emulsions of mutually immiscible solvents (e.g., water/hydrocarbons). In principle, all kinds of reaction regime leading to the polymer structures of the invention are suitable (solution polymerization, emulsion methods, precipitation methods, high-pressure methods, suspension methods, bulk polymerization, gel polymerization, and so on). Preferred suitability is possessed by precipitation polymerization, particularly preferred suitability by precipitation polymerization in tert-butanol.

The following list shows 67 copolymers suitable with particular advantage for formulating the compositions of the invention. The different copolymers 1 to 67 are obtainable in accordance with the following preparation processes 1, 2, 3, and 4.

Process 1:

These polymers can be prepared by the precipitation method in tert-butanol. The monomers were introduced in t-butanol, the reaction mixture was rendered inert, and then, after initial heating to 60° C., the reaction was initiated by addition of the corresponding t-butanol-soluble initiator (preferably dilauroyl peroxide). After the end of reaction (2 hours) the polymers were isolated by removal of the solvent under suction and by subsequent vacuum drying.

Process 2:

These polymers are preparable by the gel polymerization method in water. The monomers are dissolved in water, the reaction mixture is rendered inert, and then, after initial heating to 65° C., the reaction is initiated by addition of suitable initiators or initiator systems (preferably $Na_2S_2O_8$). The polymer gels are subsequently comminuted and the polymers are isolated after drying.

Process 3:

These polymers are preparable by the emulsion method in water. The monomers are emulsified in a mixture of water/organ. solvent (preferably cyclohexane) using an emulsifier, the reaction mixture is rendered inert by means of $N_2$, and then, after initial heating to 80° C., the reaction is initiated by addition of suitable initiators or initiator systems (preferably $Na_2S_2O_8$). The polymer emulsions are subsequently evaporated down (with cyclohexane acting as an azeotrope former for water) and the polymers are thereby isolated.

Process 4:

These polymers are preparable by the solution method in organic solvents (preferably toluene, also, for example, tertiary alcohols). The monomers are introduced in the solvent, the reaction mixture is rendered inert, and then, after initial heating to 70° C., the reaction is initiated by addition of suitable initiators or initiator systems (preferably dilauroyl peroxide). The polymers are isolated by evaporating off the solvent and by subsequent vacuum drying.

Polymers having hydrophobic side chains, uncrosslinked

| No. | Composition | Preparation process |
| --- | --- | --- |
| 1 | 95 g AMPS 5 g Genapol T-080 | 1 |
| 2 | 90 g AMPS 10 g Genapol T-080 | 1 |
| 3 | 85 g AMPS 15 g Genapol T-080 | 1 |
| 4 | 80 g AMPS 20 g Genapol T-080 | 1 |
| 5 | 70 g AMPS 30 g Genapol T-080 | 1 |

-continued

| No. | Composition | Preparation process |
| --- | --- | --- |
| 6 | 50 g AMPS 50 g Genapol T-080 | 3 |
| 7 | 40 g AMPS 60 g Genapol T-080 | 3 |
| 8 | 30 g AMPS 70 g Genapol T-080 | 3 |
| 9 | 20 g AMPS 80 g Genapol T-080 | 3 |
| 10 | 60 g AMPS 60 g BB10 | 4 |
| 11 | 80 g AMPS 20 g BB10 | 4 |
| 12 | 90 g AMPS 10 g BB10 | 3 |
| 13 | 80 g AMPS 20 g BB10 | 1 |
| 14 | 80 g AMPS 20 g Genapol LA040 | 1 |

Polymers having hydrophobic side chains, crosslinked

| No. | Composition | Preparation process |
| --- | --- | --- |
| 15 | 80 g AMPS 20 g Genapol LA040 0.6 g AMA | 1 |
| 16 | 80 g AMPS 20 g Genapol LA040 0.8 g AMA | 1 |
| 17 | 80 g AMPS 20 g Genapol LA040 1.0 g AMA | 1 |
| 18 | 628.73 g AMPS 120.45 g Genapol T-250 6.5 g TMPTA | 2 |
| 19 | 60 g AMPS 40 g BB10 1.9 g TMPTA | 4 |
| 20 | 80 g AMPS 20 g BB10 1.4 g TMPTA | 4 |
| 21 | 90 g AMPS 10 g BB10 1.9 g TMPTA | 4 |
| 22 | 80 g AMPS 20 g BB10 1.9 g TMPTA | 4 |
| 23 | 60 g AMPS 40 g BB10 1.4 g TMPTA | 4 |

Polymers having hydrophobic side chains, crosslinked, grafted

| No. | Composition | Preparation process |
| --- | --- | --- |
| 24 | 95 g AMPS 5 g BB10, 1.9 g TMPTA, 1 g Poly-NVP | 1 |
| 25 | 90 g AMPS 10 g BB10, 1.9 g TMPTA, 1 g Poly-NVP | 1 |
| 26 | 85 g AMPS 15 g BB10, 1.9 g TMPTA, 1 g Poly-NVP | 1 |
| 27 | 90 g AMPS 10 g BB10, 1.9 g TMPTA, 1 g Poly-NVP | 1 |

Polymers having silicon-containing groups, uncrosslinked

| No. | Composition | Preparation process |
| --- | --- | --- |
| 28 | 80 g AMPS, 20 g Silvet 867 | 1 |
| 29 | 80 g AMPS, 50 g Silvet 867 | 4 |

Polymers having silicon-containing groups, crosslinked

| No. | Composition | Preparation process |
| --- | --- | --- |
| 30 | 80 g AMPS, 20 g Silvet 867, 0.5 g MBA | 4 |
| 31 | 80 g AMPS, 20 g Silvet 867, 1.0 g MBA | 1 |
| 32 | 60 g AMPS, 40 g Y-12867, 0.95 g AMA | 1 |
| 33 | 80 g AMPS, 20 g Y-12867, 0.95 g AMA | 1 |
| 34 | 90 g AMPS, 10 g Y-12867, 0.95 g AMA | 1 |
| 35 | 60 g AMPS, 40 g Silvet 7280, 0.95 g AMA | 1 |
| 36 | 80 g AMPS, 20 g Silvet 7280, 0.95 g AMA | 1 |
| 37 | 90 g AMPS, 10 g Silvet 7280, 0.95 g AMA | 1 |
| 38 | 60 g AMPS, 40 g Silvet 7608, 0.95 g AMA | 1 |
| 39 | 80 g AMPS, 20 g Silvet 7608, 0.95 g AMA | 1 |
| 40 | 90 g AMPS, 10 g Silvet 7608, 0.95 g AMA | 1 |

Polymers having hydrophobic side chains and cationic groups, uncrosslinked

| No. | Composition | Preparation process |
|---|---|---|
| 41 | 87.5 g AMPS, 7.5 g Genapol T-110, 5 g DADMAC | 2 |
| 42 | 40 g AMPS, 10 g Genapol T110, 45 g methacrylamide | 2 |
| 43 | 55 g AMPS, 40 g Genapol LA040, 5 g Quat | 1 |
| 44 | 75 g AMPS, 10 g BB10, 6.7 g Quat | 1 |

Polymers having hydrophobic side chains and cationic groups, crosslinked

| No. | Composition | Preparation process |
|---|---|---|
| 45 | 60 g AMPS, 20 g Genapol T-80, 10 g Quat, 10 g HEMA | 1 |
| 46 | 75 g AMPS, 20 g Genapol T-250, 5 g Quat, 1.4 g TMPTA | 1 |
| 47 | 75 g AMPS, 20 g Genapol T-250, 10 g Quat, 1.4 g TMPTA | 1 |
| 48 | 75 g AMPS, 20 g Genapol T-250, 20 g Quat, 1.4 g TMPTA | 1 |

Polymers having fluorine-containing groups

| No. | Composition | Preparation process |
|---|---|---|
| 49 | 94 g AMPS, 2.02 g Fluowet AC 600 | 1 |
| 50 | 80 g AMPS, 20 g perfluorooctylpolyethylene glycol methacrylate, 1 g Span 80 | 3 |

Polymers having fluorine-containing groups, grafted

| No. | Composition | Preparation process |
|---|---|---|
| 51 | 80 g AMPS, 10 g Fluowet AC 600, 5 g Poly-NVP | 1 |
| 52 | 70 g AMPS, 8 g perfluorooctylethyloxyglyceryl methacrylate, 5 g Poly-NVP | 4 |

Polyfunctional polymers

| No. | Composition | Preparation process |
|---|---|---|
| 53 | 80 g AMPS, 10 g Genapol LA070, 10g Silvet 7608, 1.8 g TMPTA | 1 |
| 54 | 70 g AMPS, 5 g N-vinylpyrrolidone, 15 g Genapol T-250 methacrylate, 10 g Quat, 10 g Poly-NVP | 4 |
| 55 | 80 g AMPS, 5 g N-vinylformamide, 5 g Genapol O-150 methacrylate, 10 g DADMAC, 1.8 g TMPTA, 8 g poly-N-vinylformamide | 2 |
| 56 | 70 g AMPS, 5 g N-vinylpyrrolidone, 15 g Genapol T-250 methacrylate, 10 g Quat, 10 g Poly-NVP | 1 |
| 57 | 60 g AMPS, 10 g Genapol-BE-020 methacrylate, 10 g Genapol T-250 acrylate, 20 g Quat, 1 g Span 80 | 1 |
| 58 | 60 g AMPS, 20 g MPEG-750 methacrylate, 10 g methacryloyloxypropyldimethicone, 10 g perfluorooctylpolyethylene glycol methacrylate, 10 g poly[N-vinylcaprolactone-co-acrylic acid] (10/90) | 1 |
| 59 | 80 g AMPS, 5 g N-vinylformamide, 5 g Genapol O-150 methacrylate, 10 g DADMAC, 1.8 g TMPTA | 1 |
| 60 | 70 g AMPS, 10 g Genapol T-250 acrylate, 5 g N-methyl-4-vinylpyridinium chloride, 2.5 g Silvet Y-12867, 2.5 g perfluorohexylpolyethylene glycol methacrylate, 10 g polyethylene glycol dimethacrylate, 4 g poly[N-vinylcaprolactam] | 1 |
| 61 | 10 g AMPS, 20 g acrylamide, 30 g N-2-vinylpyrrolidone, 20 g Silvet 7608, 10 g methacryloyloxypropyldimethicone, 10 g Fluowet AC 812 | 3 |
| 62 | 60 g AMPS, 10 g DADMAC, 10 g Quat, 10 g Genapol-LA-250 crotonate, 10 g methacryloyloxypropyldimethicone, 7 g poly[acrylic acid-co-N-vinylformamide] | 1 |
| 63 | 50 g AMPS, 45 g Silvet 7608, 1.8 g TMPTA, 8 g poly[N-vinylformamide] | 1 |
| 64 | 20 g AMPS, 10 g Genapol T 110, 35 g MAA, 30 g HEMA, 5 g DADMAC | 4 |
| 65 | 20 g AMPS, 80 g BB10, 1.4 g TMPTA | 1 |
| 66 | 75 g AMPS, 20 g BB10, 6.7 g Quat, 1.4 g TMPTA | 1 |
| 67 | 35 g AMPS, 60 g acrylamide, 2 g VIFA, 2.5 g vinylphosphonic acid, 2 mol % Fluowet EA-600 | 4 |

Chemical designation of the reactants:

| | |
|---|---|
| AMPS | acryloyldimethyltaurate, either Na or NH4 salt |
| Genapol ® T-080 | $C_{16}$–$C_{18}$ fatty alcohol polyglycol ether having 8 EO units |
| Genapol ® T-110 | $C_{12}$–$C_{14}$ fatty alcohol polyglycol ether having 11 EO units |
| Genapol ® T-250 | $C_{16}$–$C_{18}$ fatty alcohol polyglycol ether having 25 EO units |
| Genapol ® LA-040 | $C_{12}$–$C_{14}$ fatty alcohol polyglycol ether having 4 EO units |
| Genapol ® LA-070 | $C_{12}$–$C_{14}$ fatty alcohol polyglycol ether having 7 EO units |
| Genapol ® O-150 methacrylate | $C_{16}$–$C_{18}$ fatty alcohol polyglycol ether methacrylate having 15 EO units |
| Genapol ® LA-250 crotonate | $C_{12}$–$C_{14}$ fatty alcohol polyglycol ether crotonate having 25 EO units |
| Genapol ® T-250 methacrylate | $C_{16}$–$C_{18}$ fatty alcohol polyglycol ether methacrylate having 25 EO units |
| Genapol ® T-250 acrylate | $C_{16}$–$C_{18}$ fatty alcohol polyglycol ether acrylate having 25 EO units |
| BB10 ® | polyoxyethylene(10)behenyl ether |
| TMPTA | trimethylolpropanetriacrylate |
| Poly-NVP | poly-N-vinylpyrrolidone |
| Silvet ® 867 | siloxane-polyalkylene oxide copolymer |
| MBA | methylenebisacrylamide |
| AMA | allyl methacrylate |
| ®Y-12867 | siloxane-polyalkylene oxide copolymer |
| Silvet ® 7608 | polyalkylene oxide-modified heptamethyltrisiloxane |
| Silvet ® 7280 | polyalkylene oxide-modified heptamethyltrisiloxane |
| DADMAC | diallyldimethylammonium chloride |
| HEMA | 2-hydroxyethyl methacrylate |
| Quat | 2-(methacryloyloxy)ethyltrimethylammonium chloride |
| Fluowet ® AC 600 | perfluoroalkylethyl acrylate |
| Span ® 80 | sorbitan ester |

The described grafting of the copolymers with other polymers, which can be carried out optionally, leads to products having a particular polymer morphology and giving rise to optically clear gels in aqueous systems. A potential disadvantage of the copolymers without grafting is a more or less strong opalescence in aqueous solution. The basis for this opalescence is hitherto unavoidable, overcrosslinked polymer fractions which arise in the course of the synthesis and are inadequately swollen in water. This produces light-scattering particles whose size is well above the wavelength of visible light and which are therefore the cause of the opalescence. The described grafting process, which can be carried out optionally, substantially reduces or entirely prevents the formation of overcrosslinked polymer fractions in relation to conventional techniques.

The described incorporation both of cationic charges and of silicon, fluorine or phosphorus atoms into the copolymers, which can be carried out optionally, leads to products which in cosmetic formulations possess particular sensorial and rheological properties. An improvement in the sensorial and rheological properties may be desired in particular in the context of use in rinse-off products (especially hair treatment compositions) or leave-on products (especially O/W emulsions).

In both crosslinked and uncrosslinked form the copolymers exhibit advantageous properties. While crosslinked systems, for example, have exhibited outstanding profiles of properties in respect of emulsion stabilization, it has been possible in particular with the aid of the uncrosslinked versions to thicken surfactant-containing solutions. The same is true of electrolyte-containing systems, which are known to be very difficult if not impossible to thicken with polyelectrolytes.

The copolymers can be used as thickeners for compositions on an aqueous or aqueous-alcoholic basis, examples being hair gels. The polymers of the invention are additionally suitable as stabilizers, dispersants, and bodying agents for aqueous surfactant preparations, examples being shampoos, shower baths, shower gels, foam baths, and the like.

The thickening action of the copolymers in aqueous surfactant compositions is boosted by an association between the polymer side chains and the surfactants, and can be controlled through the choice of the side chains of the copolymers and through the choice of the surfactants.

The suspending or dispersing and stabilizing action of the copolymers in aqueous surfactant compositions is due to the association of the polymer side chains and/or functional groups in main chain and side chain with the liquid components that are insoluble in aqueous surfactant compositions, examples being silicone oils, and/or the insoluble components, an example being zinc pyrithione.

The copolymers are likewise suitable as thickeners and dispersants, as emulsifiers, suspension media with thickening effect, and bodying agents for emulsions and suspensions, and also as lubricants, tackifiers, thickeners, dispersants and emulsifiers of decorative preparations containing solids. In this context it is also possible to use mixtures of the copolymers. The emulsifying, stabilizing and/or bodying action of the copolymers in emulsions is due to and/or boosted by an association of the polymer side chains with one another, and also by an interaction of the polymer side chains with the hydrophobic oil components.

As electrolyte, the compositions of the invention comprise salts. The salts are heteropolar compounds participants in whose crystal lattices include at least one nonhydrogen cation and at least one nonhydroxide anion. The compositions of the invention preferably comprise inorganic salts, more preferably ammonium salts or metal salts, preferably of halides, oxides, carbonates, hydrogencarbonates, phosphates, sulfates, nitrates, very preferably sodium chloride; and/or organic salts, preferably ammonium salts or metal salts, preferably of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid, galacturonic acid.

The salts are preferably derived from monovalent or polyvalent acids and bases, preferably from monovalent acids and/or monovalent bases. Particular preference is given to sodium, potassium, and ammonium salts.

As electrolyte the compositions may also comprise mixtures of different salts. The compositions contain the electrolytes normally in a concentration of from 0.01 to 50% by weight, preferably from 0.1 to 50% by weight, more preferably from 0.5 to 10% by weight.

The compositions preferably have an ionic strength I in the range from $10^{-5}$ mol/l to 2 mol/l, more preferably from $10^{-2}$ mol/l to 1 mol/l, very preferably from 0.1 mol/l to 0.75 mol/l. The ionic strength I is defined as $I=0.5\Sigma c_i*z_i^2$, where $c_i$ is the molar concentration of the individual ion types i and $z_i$ represents the ionic charges of the ion types i.

The thickening action of the comb copolymers based on acryloyldimethyltaurine is dependent on the salt concentration and copolymer concentration and on the degree of substitution of the comb copolymers. Varying the amount of salt, amount of copolymer, and degree of substitution adjusts the viscosity of the pharmaceutical and dermatological compositions.

The compositions are preferably emulsions, more preferably oil-in-water emulsions having viscosities of from 8000 mPas to 50000 mPas (RV Brookfield viscometer, 20 rpm), aqueous gels, more preferably aqueous gels comprising organic solvents having viscosities of from 15000 mPas to 100000 mPas (RV Brookfield viscometer, 20 rpm), surfactant-containing formulations, more preferably shampoos, body washes, and the like, having viscosities of from 1000 mPas to 15000 mPas (RV Brookfield viscometer, 20 rpm).

The compositions of the invention contain, based on the finished compositions, preferably from 0.01 to 10% by weight, more preferably from 0.1 to 5% by weight, very preferably from 0.5 to 3% by weight, of copolymers.

The compositions of the invention are normally adjusted to a pH in the range from 2 to 12, preferably from 3 to 8.

The compositions of the invention may comprise anionic, cationic, nonionic, zwitterionic and/or amphoteric surfactants.

The total amount of the surfactants used, based on the finished compositions, is preferably between 2 to 70% by weight, more preferably between 5 and 40% by weight, very preferably between 12 and 35% by weight.

Suitable anionic surfactants include preferably ($C_{10}$–$C_{20}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein/fatty acid condensation products, alkyl monoglyceride sulfates and sulfonates, alkylglyceride ether sulfonates, fatty acid methyltaurides, fatty acid sarcosinates, sulforicinoleates, and acylglutamates. The compounds and their mixtures are used in the form of their water-soluble or water-dispersible salts, examples being the sodium, potassium, magnesium, ammonium, mono-, di-, and triethanolammonium, and analogous alkylammonium salts.

The weight fraction of the anionic surfactants, based on the finished compositions, is preferably in the range from 2 to 30% by weight, more preferably from 5 to 25% by weight, very preferably from 12 to 22% by weight.

Suitable cationic surfactants include for example quaternary ammonium salts such as di-($C_{10}$-$C_{24}$)-alkyl-dimethylammonium chloride or bromide, preferably di-($C_{12}$–$C_{18}$)-alkyl-dimethylammonium chloride or bromide; ($C_{10}$–$C_{24}$)-alkyl-dimethylethylammonium chloride or bromide; ($C_{10}$–$C_{24}$)-alkyl-trimethylammonium chloride or bromide, preferably cetyltrimethylammonium chloride or bromide and ($C_{20}$–$C_{22}$)-alkyl-trimethylammonium chloride or bromide; ($C_{10}$–$C_{24}$)-alkyl-dimethylbenzylammonium chloride or bromide, preferably ($C_{12}$–$C_{18}$)-alkyl-dimethylbenzylammonium chloride; N-($C_{10}$–$C_{18}$)-alkyl-pyridinium chloride or bromide, preferably N-($C_{12}$–$C_{16}$)-alkyl-pyridinium chloride or bromide; N-($C_{10}$–$C_{18}$)-alkyl-isoquinolinium chloride, bromide or monoalkyl sulfate; N-($C_{12}$–$C_{18}$)-alkyl-polyoylaminoformylmethylpyridinium chloride; N-($C_{12}$–$C_{18}$)-alkyl-N-methylmorpholinium chloride, bromide or monoalkyl sulfate; N-($C_{12}$–$C_{18}$)-alkyl-N-ethylmorpholinium chloride, bromide or monoalkyl sulfate; ($C_{16}$–$C_{18}$)-alkyl-pentaoxethylammonium chloride; diisobutylphenoxyethoxyethyldimethylbenzylammonium chloride; salts of N,N-di-ethylaminoethylstearylamide and -oleylamide with hydrochloric acid, acetic acid, lactic acid, citric acid, phosphoric acid; N-acylaminoethyl-N,N-diethyl-N-methylammonium chloride, bromide or monoalkyl sulfate, and N-acylaminoethyl-N,N-diethyl-N-benzylammonium chloride, bromide or monoalkyl sulfate, acyl standing preferably for stearyl or oleyl.

The weight fraction of the cationic surfactants, based on the finished compositions, is preferably from 1 to 10% by weight, more preferably from 2 to 7% by weight, very preferably from 3 to 5% by weight.

Suitable nonionic surfactants include fatty alcohol ethoxylates (alkylpolyethylene glycols); alkylphenol polyethylene glycols; alkylmercaptan polyethylene glycols; fatty amine ethoxylates (alkylaminopolyethylene glycols); fatty acid ethoxylates (acylpolyethylene glycols); polypropylene glycol ethoxylates (Pluronics®); fatty acid alkylol amides, (fatty acid amide polyethylene glycols); N-alkyl-, N-alkoxypolyhydroxy-fatty acid amide, sucrose esters; sorbitol esters and polyglycol ethers.

The weight fraction of the nonionic surfactants is preferably from 1 to 20% by weight, more preferably from 2 to 10%, very preferably from 3 to 7% by weight.

Preferred amphosurfactants are N-($C_{12}$–$C_{18}$)-alkyl-β-aminopropionates and N-($C_{12}$–$C_{18}$)-alkyl-β-iminodipropionates as alkali metal salts and mono-, di-, and trialkylammonium salts; N-acylaminoalkyl-N,N-dimethylacetobetaine, preferably N-($C_8$–$C_{18}$)-acylaminopropyl-N,N-dimethylacetobetaine; ($C_{12}$–$C_{18}$)-alkyl-dimethylsulfopropylbetaine; amphosurfactants based on imidazoline (trade name: Miranol®, Steinapon®), preferably the sodium salt of 1-(β-carboxymethyloxyethyl)-1-(carboxymethyl)-2-laurylimidazolinium; amine oxide, e.g., ($C_{12}$–$C_{18}$)-alkyl-dimethylamine oxide, fatty acid amidoalkyldimethylamine oxide.

The weight fraction of the amphoteric surfactants is preferably in the range from 0.5 to 20% by weight, more preferably from 1 to 10% by weight.

Particularly preferred surfactants are lauryl sulfate, laureth sulfate, cocoamidopropylbetaine, sodium cocoylglutamate, and lauroamphoacetate.

In the compositions of the invention it is additionally possible to employ foam-boosting cosurfactants from the group consisting of alkylbetaines, alkylamido-betaines, aminopropionates, aminoglycinates, imidazolinium betaines, and sulfobetaines, amine oxides and fatty acid alkanol amides or polyhydroxyamides.

As further auxiliaries and additives the compositions of the invention may comprise oily substances, emulsifiers and coemulsifiers, cationic polymers, film formers, and also other additions customary in cosmetology, such as superfatting agents, moisturizing agents, stabilizers, active biogenic substances, glycerol, preservatives, pearlizing agents, dyes and fragrances, solvents, hydrotropic agents, opacifiers, further thickeners and dispersants, and also protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes and carrier substances, antioxidants, UV light protection filters, pigments and metal oxides, and antimicrobial agents.

An oily substance is any fatty substance which is liquid at room temperature (25° C.).

The fatty phase may therefore comprise one or more oils selected preferably from the following oils:

silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, and coconut oil;

synthetic oils such as purcellin oil, isoparaffins, linear and/or branched fatty alcohols and fatty acid esters, preferably guerbet alcohols having 6 to 18, preferably 8 to 10, carbon atoms; esters of linear ($C_6$–$C_{13}$) fatty acids with linear ($C_6$–$C_{20}$) fatty alcohols; esters of branched ($C_6$–$C_{13}$) carboxylic acids with linear ($C_6$–$C_{20}$) fatty alcohols, esters of linear ($C_6$–$C_{18}$) fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on ($C_6$–$C_{10}$) fatty acids;

esters such as dioctyl adipates, diisopropyl dimer dilinoleates; propylene glycols/dicaprylates or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned compounds.

Suitable nonionogenic coemulsifiers include adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; ($C_{12}$–$C_{18}$) fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-hydroxystearate, for example. Likewise suitable are mixtures of compounds from one or more of these classes of substance.

Examples of suitable ionogenic coemulsifiers include anionic emulsifiers, such as mono-, di- or tri-phosphoric esters, but also cationic emulsifiers such as mono-, di-, and tri-alkyl quats and their polymeric derivatives.

Suitable cationic polymers include those known under the INCI designation "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37&mineral oil&PPG tridecyth (Salcare SC95), PVP-dimethylaminoethyl methacrylate copolymer, guar-hydroxypropyltriammonium chlorides, and also calcium alginate and ammonium alginate. It is additionally possible to employ cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

Examples of suitable silicone compounds are dimethylpolysiloxane, methylphenylpolysiloxanes, cyclic silicones, and amino-, fatty acid-, alcohol-, polyether-, epoxy-, fluoro- and/or alkyl-modified silicone compounds, and also polyalkylsiloxanes, polyalkylarylsiloxanes, polyethersiloxanes, as described in U.S. Pat. No. 5,104,645 and the documents cited therein, which at room temperature may be present either in liquid form or in resin form.

Suitable film formers, depending on the intended application, include salts of phenylbenzimidazolesulfonic acid, water-soluble polyurethanes, for example, $C_{10}$-polycarbamyl polyglyceryl esters, polyvinyl alcohol, polyvinylpyrrolidone, copolymers thereof, for example vinylpyrrolidone/vinyl acetate copolymer, water-soluble acrylic acid polymers/copolymers and their esters or salts, examples being partial ester copolymers of acrylic/methacrylic acid and polyethylene glycol ethers of fatty alcohols, such as acrylate/steareth-20 methacrylate copolymer, water-soluble cellulose, examples being hydroxymethylcellulose, hydroxyethylcellulose, hydroxypropylcellu lose, water-soluble quaterniums, polyquaterniums, carboxyvinyl polymers, such as carbomers and their salts, polysaccharides, polydextrose for example, and glucan.

As superfatting agents it is possible to use substances such as, for example, polyethoxylated lanolin derivatives, lecithin derivatives, polyol fatty acid esters, monoglycerides, and fatty acid alkanol amides, the latter serving simultaneously as foam stabilizers. Moisturizers available include for example isopropyl palmitate, glycerol and/or sorbitol.

As stabilizers it is possible to use metal salts of fatty acids, such as magnesium, aluminum and/or zinc stearate, for example.

Active biogenic substances are to be understood as including, for example, plant extracts and vitamin complexes.

Additionally, the compositions of the invention may comprise organic solvents. Suitable organic solvents include in principle all monohydric or polyhydric alcohols. Preference is given to using alcohols having 1 to 4 carbon atoms such as ethanol, propanol, isopropanol, n-butanol, isobutanol, t-butanol, glycerol, and mixtures of said alcohols. Further preferred alcohols are polyethylene glycols having a relative molecular mass of less than 2 000. Particular preference is given to the use of polyethylene glycol having a relative molecular mass of between 200 and 600 in amounts of up to 45% by weight and of polyethylene glycol having a relative molecular mass of between 400 and 600 in amounts of from 5 to 25% by weight. Further suitable solvents are, for example, triacetin (glyceryl triacetate) and 1-methoxy-2- propanol. A hydrotropic action is developed by short-chain anionic surfactants, especially arylsulfonates, for example, cumene sulfonate or toluene sulfonate.

The compositions of the invention can be blended with conventional ceramides, pseudoceramides, fatty acid N-alkylpolyhydroxyalkyl amides, cholesterol, cholesterol fatty acid esters, fatty acids, triglycerides, cerebrosides, phospholipids, and similar substances as a care additive.

Examples of suitable preservatives include phenoxyethanol, parabens, pentanediol or sorbic acid.

As dyes it is possible to use the substances which are suitable and approved for cosmetic purposes.

Suitable active antifungal substances (fungicides) include preferably ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrithione, and octopirox.

In one preferred embodiment the compositions are rinse-off products, more preferably shampoos, body washes, shower gels, and foam baths. Modern rinse-off products frequently have a high proportion of active conditioning substances, which may also be in the form of oily fractions. Consequently, these compositions may be present as emulsions.

In another preferred embodiment the compositions are leave-on products, preferably in the form of emulsions, more preferably skincare agents, day creams, night creams, beauty creams, nutrient creams, body lotions, ointments, sun protection compositions, lipcare compositions, and deodorants.

They are also suitable, furthermore, for surfactant-free aqueous compositions and emulsions, for example, for hair cures and hair rinses, hair gels, and also permanent waving compositions, hair-coloring compositions, and for decorative cosmetics, examples being makeups, eye shadows, lipsticks, mascara, and the like.

A key point of the invention is that the compositions of the invention can be used even in the absence of an additional coemulsifier and/or bodying agent. The additional use of coemulsifiers and/or bodying agents is accordingly not mandatory, although naturally it is possible. Combination with other known coemulsifiers and/or bodying agents may be desirable in order to set specific cosmetic profiles and to exploit synergistic effects.

The examples which follow serve to illustrate the invention, though without restricting it (all percentages are by weight). The copolymers used in the examples are representatives of the particularly preferred copolymers 1 to 67 already listed in the description. The copolymers were prepared by the therein-indicated processes 1, 2 using the preferred initiators and solvents.

Thickener performance as a function of electrolyte concentration

Use concentration of polymer in water: 10% by weight

| Polymer I: | 100 g AMPS + 0 g Genapol LA 070 |
| Polymer II: | 90 g AMPS + 10 g Genapol LA 070 |
| Polymer III: | 80 g AMPS + 20 g Genapol LA 070 |

These polymers were prepared by the precipitation method in tert-butanol (process 1) and were used in the form of the ammonium salt.

The viscosity was measured using an RV-Brookfield viscometer (spindle as per table), 20 rpm, 20° C.

The unsubstituted, comparative polymer I exhibits no viscosity in aqueous solution. The inventive polymers II and III significantly thicken aqueous systems. The thickening action is dependent on the salt concentration and on the degree of substitution. Transparent gels are obtained.

Formulation Examples

EXAMPLE 1

O/W Skin Milk with Thermal Water

Composition:

| A | Copolymer No. 21 | 1.50% |
| B | Isopropyl palmitate | 4.00% |
|   | Almond oil | 4.00% |
|   | Wheatgerm oil | 1.00% |
|   | ® Cetiol SN (Henkel) Cetearyl isononanoate | 8.00% |
| C | Thermal water | ad 100% |
| D | Fragrances | 0.30% |

Preparation
I Disperse A in B with stirring.
II Add C and D successively to I.
III Homogenize emulsion.

Examples of Surfactant Formulations

EXAMPLE 2

Shower Bath with Dead Sea Salt

| | Composition | |
|---|---|---|
| A | ® GENAPOL LRO liquid (Clariant) Laureth sulfate, Na salt | 40.00% |
| B | Fragrance | 0.30% |

TABLE 1

Thickening action of polymer in aqueous solution as a function of electrolyte concentration

| | [% by weight NaCl] | | | | | | | |
|---|---|---|---|---|---|---|---|---|
| | 0.0% | 1.0% | 2.0% | 3.0% | 4.0% | 5.0% | 6.0% | 7.0% |
| Polymer I | 914 | 506 | 454 | 402 | 336 | 310 | 282 | 276 |
| Spindle | 2 | 2 | 2 | 2 | 2 | 2 | 2 | 2 |
| Polymer II | 2260 | 1620 | 1725 | 2010 | 2200 | 2555 | 2845 | 3370 |
| Spindle | 3 | 3 | 3 | 3 | 3 | 3 | 3 | 3 |
| Polymer III | 8050 | 11100 | 16900 | 21600 | 32600 | 38400 | 47000 | 62200 |
| Spindle | 4 | 5 | 6 | 7 | 7 | 7 | 7 | 7 |

-continued

| | Composition | |
|---|---|---|
| C | Water | 52.70% |
| | Sodium chloride | 10.0% |
| D | Dye | q.s. |
| | Preservative | q.s. |
| | ® GENAGEN LDA (Clariant) Lauroamphodiacetate, Na salt | 6.00% |
| | Citric acid | q.s. |
| E | Copolymer No. 1 | 1.00% |

Preparation

I Stir B into A.
II Mix the components of C.
III Add components from D successively to II.
IV Adjust the viscosity by stirring E into II.

What is claimed is:

1. An electrolyte-containing cosmetic, dermatological or pharmaceutical composition comprising an electrolyte and which comprises at least one copolymer obtained by free-radical copolymerization of
   A) acryloyldimethyltaurine and/or acryloyldimethyltaurates,
   B) optionally, one or more further olefinically unsaturated, noncationic, comonomer which has at least one oxygen, nitrogen, sulfur or phosphorus atom and has a molecular weight of less than 500 g/mol,
   C) optionally, one or more olefinically unsaturated, cationic comonomer which has at least one oxygen, nitrogen, sulfur or phosphorus atom and has a molecular weight of less than 500 g/mol,
   D) optionally, one or more silicon-containing component capable of free-radical polymerization and having a functionality of at least one,
   E) optionally, one or more fluorine-containing component capable of free-radical polymerization and having a functionality of at least one,
   F) optionally, one or more olefinically mono- or polyunsaturated, macromonomer each possessing at least one oxygen, nitrogen, sulfur or phosphorus atom and having a number-average molecular weight of greater than or equal to 200 g/mol, the macromonomer not being a silicon-containing component D) or fluorine-containing component E), and where the at least one macromonomer is of formula (IV)

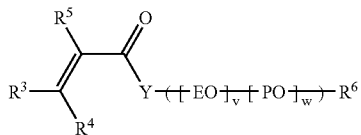

(IV)

in which
   $R_3$, $R_4$, $R_5$, and $R_6$ independently of one another are hydrogen or n-aliphatic, iso-aliphatic, olefinic, cycloaliphatic, arylaliphatic or aromatic ($C_1$–$C_{30}$) hydrocarbon radicals,
   v and w independently of one another are from 0 to 500, the sum of v and w is on average $\leq 1$, and
   V is a bridge selected from the group consisting of —O—, —C(O)—, —C(O)—O—, —S—, —O—CH$_2$—CH(O—)—CH$_2$OH, —O—CH(OH)—CH$_2$O—, —O—SO$_2$—O—, —O—SO$_2$—O—, —O—SO—O—, —PH—, —P(CH$_3$)—, —PO$_3$—, —NH—, and —N(CH$_3$)—,
   G) optionally, the copolymerization taking place in the presence of at least one polymeric additive having number-average molecular weights of from 200 g/mol to $10^9$ g/mol,
   H) with the proviso that component A) is copolymerized with at least one component selected from one of component D) to G).

2. The electrolyte-containing composition as claimed in claim 1, wherein the comonomer B) is selected from the group consisting of unsaturated carboxylic acids, salts of unsaturated carboxylic acids, anhydrides of unsaturated carboxylic acids, esters or unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof, methallylsulfonic acid or the esters or salts thereof, and mixtures thereof.

3. The electrolyte-containing composition as claimed in claim 1, wherein the monomer C) is selected from the group consisting of diallyldimethylammonium chloride (DADMAC),
   [2-(methacryloyloxy)ethyl]trimethylammonium chloride (MAPTAC),
   [2-(acryloyloxy)ethyl]trimethylammonium chloride,
   [2-methacrylamidoethyl]trimethylammonium chloride,
   [2-(acrylamido)ethyl]trimethylammonium chloride,
   N-methyl- 2-vinylpyridinium chloride,
   N-methyl- 4-vinylpyridinium chloride,
   dimethylaminoethyl methacrylate,
   dimethylaminopropylmethacrylamide,
   methacryloylethyl N-oxide,
   methacryloylethylbetaine, and mixtures thereof.

4. The electrolyte-containing composition of claim 1, wherein the silicon-containing components D) are compounds of the formula (I)

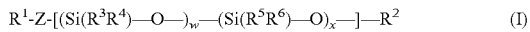

(I)

where
   $R^1$ represents a radical selected from the group consisting of vinyl, allyl, methallyl, methylvinyl, acryloyl, methacryloyl, crotonyl, senecionyl, itaconyl, maleyl, fumaryl, and styryl;
   Z is a chemical bridge,
   $R^3$, $R^4$, $R^5$, and $R^6$ independently of one another are —CH$_3$, —O—CH$_3$, —C$_6$H$_5$ or —O—C$_6$H$_5$;
   w, x denote numbers from 0 to 500, it being necessary for either w or x to be greater than zero; and
   $R^2$ is a saturated or unsaturated aliphatic, cycloaliphatic, arylaliphatic or aromatic radical having in each case 1 to 50 carbon atoms or a group of the formulae —OH, —NH$_2$, —N(CH$_3$)$_2$, —R$^7$ or a group -Z-R$^1$, where Z and R$^1$ have the meanings mentioned above, and
   $R^7$ is selected from the group consisting of —O—Si(CH$_3$)$_3$, —O—Si(phenyl)$_3$, —O—Si(O—Si(CH$_3$)$_3$)$_2$ CH$_3$) and
   —O—Si(O—Si(phenol)$_3$)$_2$phenol.

5. The electrolyte-containing composition of claim 1, wherein the fluorine-containing components E) are compounds of the formula (II)

$$R^1-Y-C_rH_{2r}C_sF_{2s}CF_3 \quad (II)$$

where
R$^1$ represents a polymerizable function from a vinylically unsaturated compound;
Y is a chemical bridge, and
r, s are stoichiometric coefficients which independently of one another are numbers between 0 and 200.

6. The electrolyte-containing composition of claim 1, wherein component F) comprises besides the macromonomer of formula (IV) additionally one or more macromonomer of formula (III)

$$R^1\text{-}Y\text{-}[(A)_v\text{-}(B)_w\text{-}(C)_x\text{-}(D)_z]-R^2 \quad (III)$$

where R$^1$ represents a polymerizable function from a vinylically unsaturated compound;
Y is a bridging group,
A, B, C, and D independently of one another are discrete chemical repeating units;
v, w, x, and z independently of one another amount to from 0 to 500, the sum of v, w, x, and z being on average $\leq 1$; and
R$^2$ is a linear or branched aliphatic, olefinic, cycloaliphatic, arylaliphatic or aromatic ($C_1$–$C_{50}$) hydrocarbon radical, OH, —NH$_2$ or —N(CH$_3$)$_2$ or is [—Y—R$^1$].

7. The electrolyte-containing composition of claim 1, wherein the polymeric additive G) is selected from the group consisting of polyalkylene glycol, alkylpolyglycol, and mixtures thereof or a homopolymer or copolymer of a compound selected from the group consisting of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC) and/or [2-(methacryloyloxy)ethyl]trimethylammonium chloride (MAPTAC), and mixtures thereof.

8. The electrolyte-containing composition of claim 1, wherein said copolymerization takes place in the presence of at least one polymeric additive G).

9. The electrolyte-containing composition of claim 1, wherein the copolymer is crosslinked.

10. The electrolyte-containing composition of claim 1, wherein the copolymer is prepared by precipitation polymerization in tert-butanol.

11. The electrolyte-containing composition of claim 1, wherein the copolymer is water-soluble or water-swellable.

12. The electrolyte-containing composition of claim 1 which comprises, based on a finished composition, from 0.01 to 10% by weight of the copolymer.

13. The electrolyte-containing composition of claim 1, which comprises as electrolytes salts.

14. The electrolyte-containing composition of claim 1, wherein the electrolyte comprises inorganic salts.

15. The electrolyte-containing composition of claim 1, wherein an electrolyte concentration is from 0.01 to 50% by weight.

16. The electrolyte-containing composition of claim 1, wherein an ionic strength I is in the range from 10$^{-5}$ mol/l to 2 mol/l.

17. The electrolyte-containing composition of claim 1, which is an emulsion.

18. The electrolyte-containing composition of claim 1, which is an aqueous gel.

19. The electrolyte-containing composition of claim 1, which is a surfactant-containing formulation.

20. The electrolyte-containing composition of claim 1, which is a rinse-off composition.

21. The electrolyte-containing composition of claim 1, which is a leave-on product.

22. The electrolyte-containing composition of claim 1, which comprises at least one copolymer obtained by copolymerizing at least components A), B), and F).

23. The electrolyte-containing cosmetic, dermatological or pharmaceutical composition of claim 4 wherein the chemical bridge Z is selected from the group consisting of —O—, —O—(($C_1$–$C_{50}$)alkylene)-, —O—(($C_6$–$C_{30}$) arylene)-, —O—(($C_5$–$C_8$)cycloalkylene)-, —O—(($C_1$–$C_{50}$) alkenylene-, -polypropylene oxide)$_n$-, -(polyethylene oxide)$_o$-, -(polypropylene oxide)$_n$(polyethylene oxide)$_o$-, and mixtures thereof where n and o independently of one another denote numbers from 0 to 200 and the distribution of EO/PO units can be random or in block form.

24. The electrolyte-containing cosmetic, dermatological or pharmaceutical composition of claim 4 wherein the chemical bridge Z is —O—(($C_1$–$C_{50}$)alkylene)-(Si(OCH$_3$)$_2$)— or O—(Si (OCH$_3$)$_2$)—O.

25. The electrolyte-containing cosmetic, dermatological or pharmaceutical composition of claim 5 wherein, R$^1$ is a radical selected from the group consisting of vinyl, allyl, methallyl, methyvinyl, acryloyl, methacryloyl, crotonyl, senecionyl, itaconyl, maleyl, fumaryl, styryl, and mixtures thereof.

26. The electrolyte-containing cosmetic, dermatological or pharmaceutical composition of claim 5, wherein the chemical bridge Y is selected from the group consisting of —O—, —C(O)—, —C(O)—O—, —S—, —O—CH$_2$—CH (O—)—CH$_2$OH, —O—CH$_2$—CH(OH)—CH$_2$—O—, —O—SO$_2$—O—, —O—S(O)—O—, —PH—, —P(CH$_3$)—, —PO$_3$—, —NH—, —N(CH$_3$)—, —O—($C_1$–$C_{50}$)alkyl-O—, —O-phenyl-O—, —O-benzoyl-O—, —O—($C_5$–$C_8$) cycloalkyl-O—, —O—($C_1$–$C_{50}$)alkenyl-O—, —O—(CH(CH$_3$)—CH$_2$—O)$_n$—, —O—(CH$_2$—CH$_2$—O)$_n$—, —O—([CH—CH$_2$—O]$_n$—[CH$_2$—CH$_2$—O]$_m$)$_o$—, where n, m, and o independently of one another denote numbers from 0 to 200, and mixtures thereof.

27. The electrolyte-containing cosmetic, dermatological or pharmaceutical composition of claim 5 wherein, R$^1$ is a radical selected from the group consisting of a vinyl, allyl, methallyl, methylvinyl, acryloyl, methacryloyl, crotonyl, senecionyl, itaconyl, maleyl, fumaryl, styryl, and mixtures thereof.

28. The electrolyte-containing cosmetic, dermatological or pharmaceutical composition of claim 6, wherein the bridging group Y is selected from the group consisting of —O—, —S—, —C(O)—, —C(O)—O—, —O—CH$_2$—CH (O—)—CH$_2$OH, —O—CH$_2$—CH(OH)—CH$_2$O—, —O—SO$_2$—O—, —O—SO—O—, —PH—, —P(CH$_3$)—, —PO$_3$—, —NH—, —N(CH$_3$)—, and mixtures thereof.

29. The electrolyte-containing cosmetic, dermatological or pharmaceutical composition of claim 6 wherein the discrete repeating units of A, B, C, and D are originating from a unit selected from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

30. The electrolyte-containing cosmetic, dermatological or pharmaceutical composition of claim 6 wherein the discrete repeating units of A, B, C, and D are originating from a unit of ethylene oxide or propylene oxide.

31. The electrolyte-containing cosmetic, dermatological or pharmaceutical composition of claim 6, wherein v, w, x, and z independently of one another amount to from 1 to 30.

32. The electrolyte-containing cosmetic, dermatological or pharmaceutical composition of claim 6 wherein, $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

33. The electrolyte-containing cosmetic, dermatological or pharmaceutical composition of claim 15, wherein the electrolyte concentration is from 0.1 to 50% by weight of the copolymer.

34. The electrolyte-containing cosmetic, dermatological or pharmaceutical composition of claim 15, wherein the electrolyte concentration is from 0.5 to 10 % by weight of the copolymer.

35. The electrolyte-containing cosmetic, dermatological or pharmaceutical composition of claim 16, wherein the ionic strength I is in the range of $10^{-2}$ to 1 mol/l.

36. The electrolyte-containing cosmetic, dermatological or pharmaceutical composition of claim 16, wherein the ionic strength I is in the range of 0.1 mol/l to 0.75 mol/l.

37. The electrolyte-containing cosmetic, dermatological or pharmaceutical composition of claim 17, wherein said composition is an oil in water emulsion having a viscosity of from 8,000 mPas to 50,000 mPas.

38. The electrolyte-containing cosmetic, dermatological or pharmaceutical composition of claim 18, wherein the aqueous gel compilses organic solvent and has a viscosity of from 15,000 mPas to 100,000 mPas.

39. The electrolyte-containing cosmetic, dermatological or pharmaceutical composition of claim 18, wherein the aqueous gel comprises organic solvent.

40. The electrolyte-containing cosmetic, dermatological or pharmaceutical composition of claim 19, wherein the surfactant-containing formulation is a shampoo or a body wash having a viscosity of from 1000 mPas to 15,000 mPas.

41. An electrolyte-containing cosmetic, dermatological or pharmaceutical composition which comprises an electrolyte and comprises at least one copolymer obtained by free-radical copolymerization of acryloyldimethyltaurine and/or acryloyldimethyltaurate, with or in the presence of at least one component selected from the group consisting of:

a) one or more silicon-containing component capable of free-radical polymerization and having a functionality of at least one, b) one or more fluorine-containing component capable of free-radical polymerization and having a functionality of at least one, c) one or more olefinically mono- or polyunsaturated, macromonomer each possessing at least one oxygen, nitrogen, sulfur or phosphorus atom and having a number-average molecular weight of greater than or equal to 200 g/mol, the macromonomer not being the silicon-containing component a) or the fluorine-containing component b), and d) at least one polymeric additive having number-average molecular weights of from 200 g/mol to $10^9$ g/mol.

42. The acidic cosmetic, dermatological or pharmaceutical composition of claim 41, wherein said at least one component is selected from the group consisting of a) through d) and e) one or more further olefinically unsaturated, noncationic comonomer which have at least one oxygen, nitrogen, sulfur or phosphorus atom and possess a molecular weight of less than 500 g/mol, or f) one or more olefinically unsaturated, cationic comonomer which has at least one oxygen, nitrogen, sulfur or phosphorus atom and possess a molecular weight of less than 500 g/mol, and mixtures thereof.

43. The electrolyte-containing cosmetic, dermatological or pharmaceutical composition of claim 41 wherein said macromonomer c) is crosslinking.

44. The electrolyte-containing cosmetic, dermatological or pharmaceutical composition of claim 42, wherein said olefinically unsaturated, noncationic comonomer e) is crosslinking.

* * * * *